US011434196B2

(12) United States Patent
Vasireddi et al.

(10) Patent No.: US 11,434,196 B2
(45) Date of Patent: Sep. 6, 2022

(54) PROCESS FOR PREPARATION OF 2-AMINO-5-HYDROXY PROPIOPHENONE

(71) Applicant: LAURUS LABS LIMITED, Hyderabad (IN)

(72) Inventors: Uma Maheswer Rao Vasireddi, Hyderabad (IN); Venkata Ramana Kintali, Visakhapatnam (IN); Jagadeeswara Rao Dadi, Visakhapatnam (IN); Raj Koti Katkuri, Visakhapatam (IN); Sridhar Tummu, Visakhapatnam (IN)

(73) Assignee: Laurus Labs Limited, Hyderabad (IN)

( * ) Notice: Subject to any disclaimer, the term of this patent is extended or adjusted under 35 U.S.C. 154(b) by 0 days.

(21) Appl. No.: 17/419,378

(22) PCT Filed: Jan. 14, 2020

(86) PCT No.: PCT/IB2020/050256
§ 371 (c)(1),
(2) Date: Jun. 29, 2021

(87) PCT Pub. No.: WO2020/148641
PCT Pub. Date: Jul. 23, 2020

(65) Prior Publication Data
US 2022/0081388 A1    Mar. 17, 2022

(30) Foreign Application Priority Data
Jan. 15, 2019  (IN) .............................. 201941001793

(51) Int. Cl.
*C07C 221/00*    (2006.01)
*C07D 491/147*    (2006.01)

(52) U.S. Cl.
CPC ........ *C07C 221/00* (2013.01); *C07D 491/147* (2013.01)

(58) Field of Classification Search
CPC .. C07C 225/22; C07C 221/00; C07D 491/147
See application file for complete search history.

(56) References Cited

U.S. PATENT DOCUMENTS

| 6,121,451 | A | 9/2000 | Henegar et al. | |
|---|---|---|---|---|
| 6,689,922 | B1 * | 2/2004 | Bernardon | A61P 37/02 568/744 |
| 7,126,000 | B2 * | 10/2006 | Ogawa | C07C 205/44 546/92 |
| 7,608,740 | B2 * | 10/2009 | Rao | C07C 201/12 564/418 |
| 2004/0106830 | A1 * | 6/2004 | Ogawa | C07D 491/04 568/424 |
| 2008/0221358 | A1 * | 9/2008 | Rao | C07C 221/00 564/418 |

FOREIGN PATENT DOCUMENTS

| CN | 101362701 A | * | 2/2009 | |
|---|---|---|---|---|
| CN | 101723841 A | * | 6/2010 | |
| CN | 101723841 B | | 3/2012 | |
| CN | 104803861 A | * | 7/2015 | |
| CN | 108794737 B | * | 7/2019 | ......... A61L 26/0052 |
| GB | 711905 A | * | 7/1954 | |

OTHER PUBLICATIONS

CAS Abstract and Indexed Compounds, Z. Liu et al., CN 104803861 (2015) (Year: 2015).*
A. Rao et al., 43 Synthetic Communications, 1661-1667 (2013) (Year: 2013).*
CASREACT Abstract and Indexed Reactions, X. Yang et al., CN 108794737 (2018) (Year: 2018).*
A. Ejima et al., 40 Chemical & Pharmaceutical Bulletin, 683-688 (1992) (Year: 1992).*
CAS Registry No. 1557589-39-5 (Feb. 27, 2014) (Year: 2014).*
CAS Abstract and Indexed Compound, J. Bernardon U.S. Pat. No. 6,689,922 (2004) (Year: 2004).*
Ruben Bardanyan et al., "Synthesis of Essential Drugs", 1$^{st}$ Edition, Ruben, Mar. 10, 2006.
Xiao-Dong Xiong et. al. in *Organic Preparations and Procedures International*, 41, 423-427, 2009.
Aurore et al. in *Bioorganic & Medicinal Chemistry Letters* vol. 14, issue 9, pp. 2363-20 2365, 2004.

* cited by examiner

*Primary Examiner* — Alexander R Pagano
(74) *Attorney, Agent, or Firm* — Blank Rome LLP

(57) ABSTRACT

The present invention relates to a process for preparation of 2-Amino-5-hydroxy propiophenone, a key intermediate for the synthesis of camptothecin analogs including 7-Ethyl-10-hydroxycamptothecin (SN-38).

31 Claims, No Drawings

PROCESS FOR PREPARATION OF 2-AMINO-5-HYDROXY PROPIOPHENONE

CROSS-REFERENCE TO RELATED APPLICATIONS

This is a national phase application that is based on and claims the benefit of International Application No. PCT/IB2020/050256, filed on Jan. 14, 2020, which is based on and claims the benefit under Indian Provisional Application No. 201941001793, filed on Jan. 15, 2019, entitled "Process for preparation of 2-Amino-5-hydroxy propiophenone", the contents of which are incorporated by reference herein.

FIELD OF THE INVENTION

The present invention generally relates to a process for preparation of 2-Amino-5-hydroxy propiophenone, a key intermediate in the synthesis of camptothecin analogs including 7-Ethyl-10-hydroxycamptothecin (SN-38).

BACKGROUND OF THE INVENTION

2-Amino-5-hydroxy propiophenone is an important intermediate useful in the preparation of 7-Ethyl-10-hydroxycamptothecin (SN-38), which is a crucial intermediate in preparation of an antineoplastic class of agent Irinotecan {(4S)-4,11-diethyl-4-hydroxy-9-[(4-piperidinopiperidino)carbonyloxy]-1H-pyrano[3',4':6,7]indolizino[1,2-b]quinoline-3,14(4H,12H) dione}.

Irinotecan is most commonly used to treat metastatic carcinoma. When administered to a patient, irinotecan metabolizes to a more active metabolite, 7-ethyl-10-hydroxycamptothecin (SN-38). Structural formula of these compounds is represented as follows:

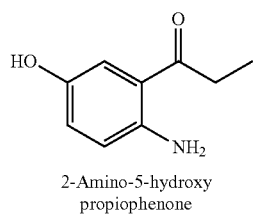

2-Amino-5-hydroxy propiophenone
(Formula I)

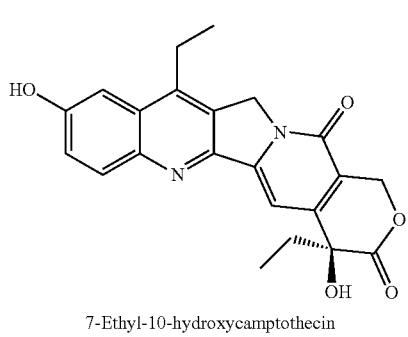

7-Ethyl-10-hydroxycamptothecin
(SN-38)

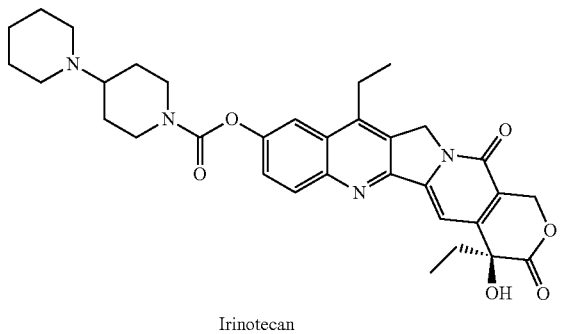

Irinotecan

Various methods for the synthesis of 7-Ethyl-10-hydroxycamptothecin (SN-38) and subsequent conversion in to Irinotecan is known in the art. One of the best method known till now is to synthesize the two key intermediates, which are 2-Amino-5-hydroxy propiophenone of Formula I and tricyclic ketone intermediates and subsequent condensation of these two compounds by Friedlander reaction to give 7-ethyl-10-hydroxycamptothecin (SN-38) and then converting SN-38 in to Irinotecan (Reference: U.S. Pat. No. 6,121,451) and the process schematically represented as follows:

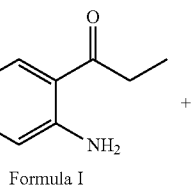

Formula I

+

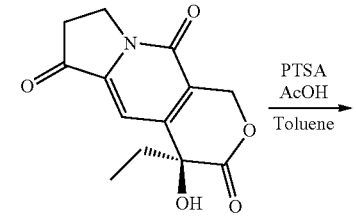

Tricyclic ketone intermediate

PTSA
AcOH
Toluene

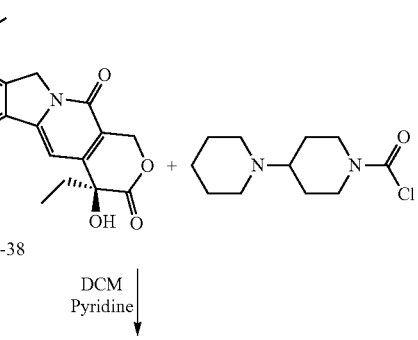

SN-38

DCM
Pyridine

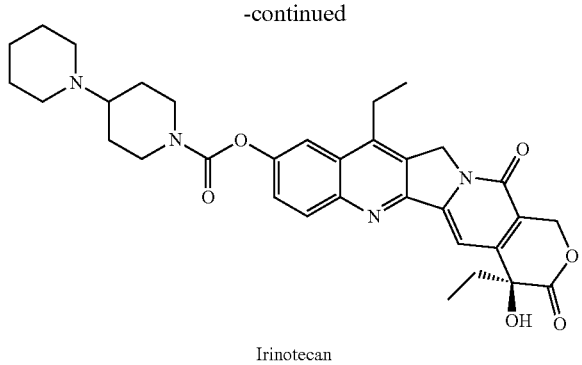

Irinotecan

2-Amino-5-hydroxy propiophenone of Formula I is one of the key intermediate in the preparation of 7-ethyl-10-hydroxycamptothecin (SN-38). Till date many literatures have described the preparation of 2-Amino-5-hydroxy propiophenone of Formula I and all these references suffers from various draw backs, which includes low reaction selectivity, involves hazardous reactions and getting less yields with low purity. The reported literature on the preparation of formula I described as below:

U.S. Pat. No. 7,126,000 ("the '000 patent") discloses a process for preparation of 2-Amino-5-hydroxy propiophenone of Formula I from either 5-hydroxy-2-nitrobenzaldehyde or from 5-benzyloxy-2-nitrobenzaldehyde. The process disclosed in the '000 patent is schematically represented as follows:

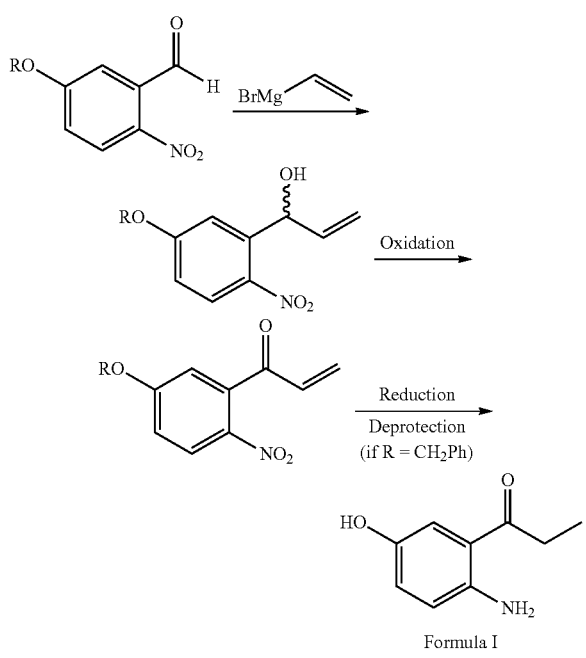

R = H
R = CH₂Ph

The process disclosed under the '000 patent involves use of 5-hydroxy-2-nitrobenzaldehyde or its protected derivative as a starting material and subsequent conversion of this intermediate in to Formula I involves many tedious reaction steps, for example usage of highly sensible Grignard reactions and reduction of alkene chain. The usage of starting material aldehyde compound is considerably expensive and formation of impurities during the Grignard and final reduction stage, which makes the process tedious and uneconomical.

U.S. Pat. No. 7,608,740 ("the '740 patent") discloses a process for the preparation of 2-Amino-5-hydroxy propiophenone of Formula I from 3-fluoro propiophenone. The process disclosed in the '740 patent is schematically represented as follows:

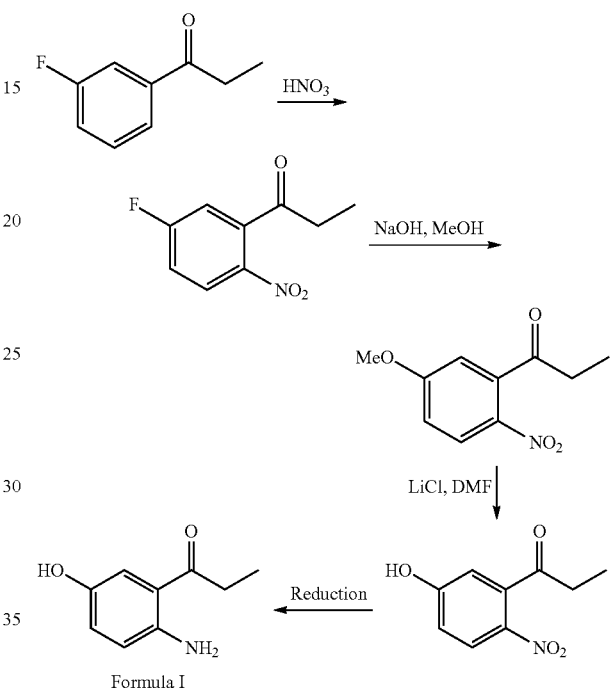

Formula I

The process disclosed under the '740 patent mainly involves nitration of 5-fluoro propiophenone using nitric acid. While doing nitration reaction there is always possibility of nitro group substitution at ortho and/or para positions of the ring instead of single para group as required and this leads to contamination of the product with para substituted compounds and therefore cumbersome chromatography purifications are required to purify the product.

Chinese Patent number CN101723841B ("the '841 patent") discloses a process for the preparation of 2-Amino-5-hydroxy propiophenone of Formula I from 3-chloro propiophenone. The process disclosed in the '841 patent is schematically represented as follows:

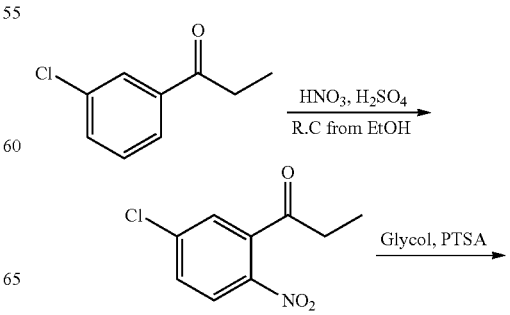

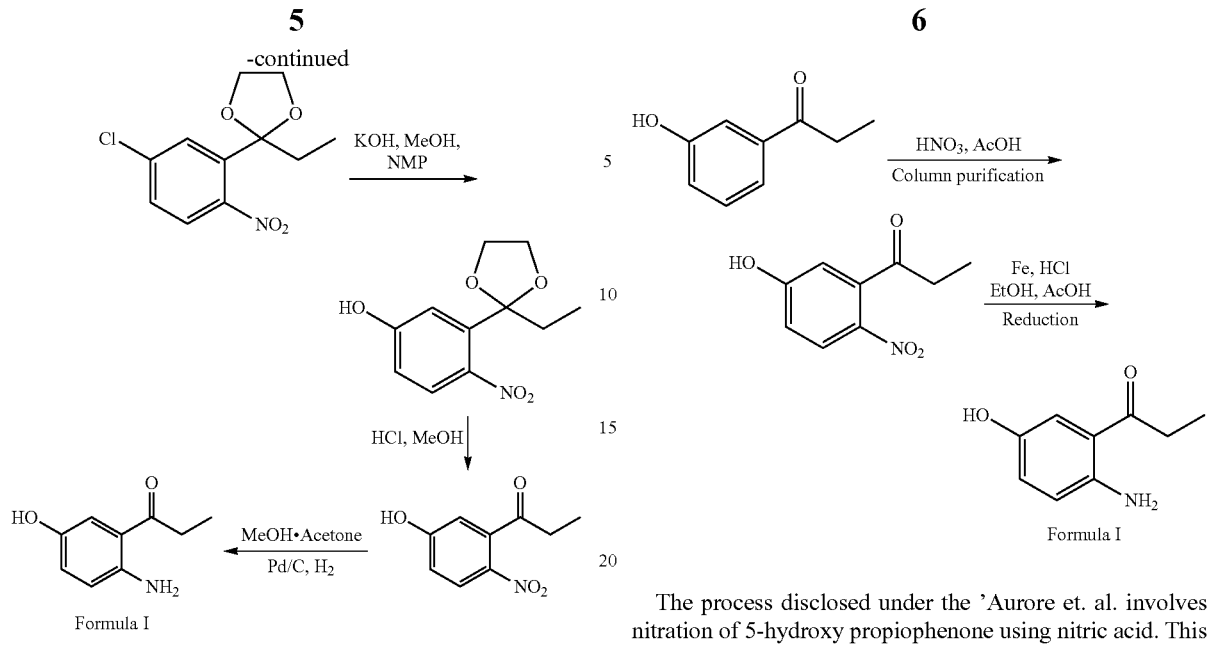

Again the process disclosed under the '841 publication suffers from formation of region isomers/positional isomers during the nitration reaction.

Xiao-Dong Xiong et. al. in *Organic Preparations and Procedures International*, 41, 423-427, 2009 discloses a process for preparation of 2-Amino-5-hydroxy propiophenone of Formula I by converting aldehyde group in to propiophenone. This process has disadvantages like, aldehyde intermediate itself is more expensive and involves several steps for converting it in to propionyl group. The process disclosed by Xiao-Dong Xiong et. al. is schematically represented as follows:

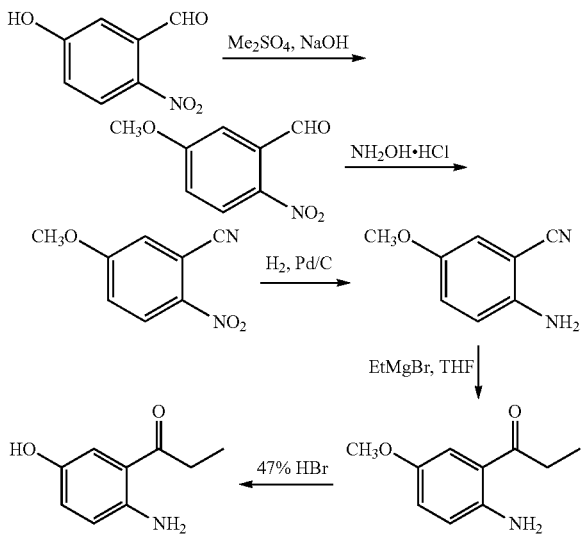

Aurore et al. in *Bioorganic & Medicinal Chemistry Letters* Volume 14, Issue 9, Pages 2363-2365, 2004 (the 'Aurore reference) discloses a process for preparation of 2-Amino-5-hydroxy propiophenone of Formula I by nitration of 3'-hydroxy propiophenone. The process disclosed by Aurore et al. is schematically represented as follows:

The process disclosed under the 'Aurore et. al. involves nitration of 5-hydroxy propiophenone using nitric acid. This process has disadvantage as it involves formation of unwanted regio isomers/positional isomers in the nitration reaction by substitution of nitro group at both ortho and para positions instead of same reaction at only para position. Removal of positional isomers by using normal purifications is always a challenging task as these are closely associated each other by its retention factor. Therefore requires multiple column purifications and even then no guarantee to getting the highly pure compound as required for the pharmaceutical use.

Based on the drawbacks mentioned above, there is a vital need to develop a process for the preparation of 2-Amino-5-hydroxy propiophenone of Formula I, which is readily amenable to large scale production.

Hence, present inventors focused research to simplify the process for the preparation of 2-Amino-5-hydroxy propiophenone of Formula I that circumvents the aforementioned drawbacks, which process involves mainly regioselective nitration to avoid/reduce the formation of regio isomers/positional isomers; thereby avoiding the cumbersome column purifications and makes the process viable for large scale manufacturing.

SUMMARY OF THE INVENTION

Accordingly, the present invention provides an improved process for the preparation of 2-Amino-5-hydroxy propiophenone of Formula I, an intermediate compound useful in the preparation of 7-Ethyl-10-hydroxycamptothecin (SN-38).

In accordance with one embodiment, the present invention provides a process for preparation of 2-Amino-5-hydroxy propiophenone of Formula I:

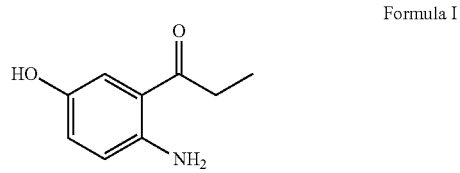

Formula I comprising:
  a) reacting a compound of Formula III with a suitable nitrating reagent to obtain a compound of Formula IV, and

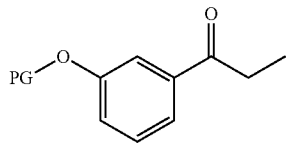
Formula III

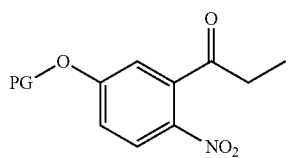
Formula IV wherein the "PG" represents a suitable hydroxyl protecting group;
  b) converting the compound of Formula IV in to 2-Amino-5-hydroxy propiophenone of Formula I.

In accordance with another embodiment, the present invention provides a process for preparation of 2-Amino-5-hydroxy propiophenone of Formula I, comprising:
a) reacting a compound of Formula III with a suitable nitrating reagent to obtain a compound of Formula IV, wherein the "PG" represents a suitable hydroxyl protecting group; and
b) converting the compound of Formula IV in to 2-Amino-5-hydroxy propiophenone of Formula I; wherein the "PG" is selected from the group comprising of trichloroethyl formate, methyl formate, ethyl formate, hexyl formate, isobutyl formate, benzyl formate, methoxymethyl, methoxyethoxymethyl, tetrahydropyranyl, tetrahydrofuran, allyl, methoxytrityl, methylthio methyl, benzyl, benzoyl, p-methoxybenzyl, t-butyldimethylsilyl, t-butyldiphenylsilyl, triisopropylsilyl, di-tert-butylsilylene, tetraisopropyldisiloxanylidene, pivaloyl and benzoyl.

In accordance with another embodiment, the present invention provides a process for preparation of 2-Amino-5-hydroxy propiophenone of Formula I:

Formula I comprising:
  a) reacting a compound Formula II with a suitable hydroxyl protecting agent to obtain a compound of Formula III; wherein "PG" represents a suitable hydroxyl protecting group,

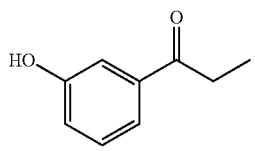
Formula II

-continued

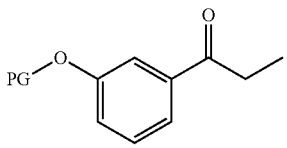
Formula III b) reacting the compound of Formula III with a suitable nitrating reagent to obtain a compound of Formula IV, and

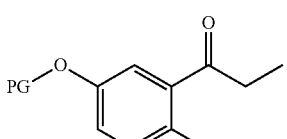
Formula IV c) converting the compound of Formula IV in to 2-Amino-5-hydroxy propiophenone of Formula I.

In accordance with another embodiment, the present invention provides a process for preparation of 2-Amino-5-hydroxy propiophenone of Formula I, comprising:

a) reacting a compound Formula II with a suitable hydroxyl protecting agent to obtain a compound of Formula III; wherein "PG" represents a suitable hydroxyl protecting group, b) reacting the compound of Formula III with a suitable nitrating reagent to obtain a compound of Formula IV, and c) converting the compound of Formula IV in to 2-Amino-5-hydroxy propiophenone of Formula I; wherein the "PG" is selected from the group comprising of trichloroethyl formate, methyl formate, ethyl formate, hexyl formate, isobutyl formate, benzyl formate, methoxymethyl, methoxyethoxymethyl, tetrahydropyranyl, tetrahydrofuran, allyl, methoxytrityl, methylthio methyl, benzyl, benzoyl, p-methoxybenzyl, t-butyldimethylsilyl, t-butyldiphenylsilyl, triisopropylsilyl, di-tert-butylsilylene, tetraisopropyldisiloxanylidene, pivaloyl and benzoyl.

In accordance with another embodiment, the present invention provides a process for preparation of 2-Amino-5-hydroxy propiophenone of Formula I:

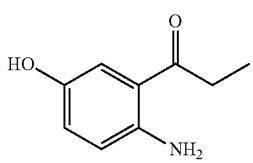
Formula I comprising:
  a) reacting a compound Formula II with a suitable hydroxyl protecting agent to obtain a compound of Formula III; wherein "PG" represents a suitable hydroxyl protecting group, Formula II

[Structure: 3-hydroxypropiophenone — HO-phenyl-C(=O)-CH2CH3]

Formula III

[Structure: PG-O-phenyl-C(=O)-CH2CH3]

b) reacting the compound of Formula III with a suitable nitrating reagent to obtain a compound of Formula IV, Formula IV

[Structure: PG-O-phenyl(with NO2)-C(=O)-CH2CH3]

c) deprotecting the compound of Formula IV with a suitable deprotecting agent to obtain a compound of Formula V, and Formula V

[Structure: HO-phenyl(with NO2)-C(=O)-CH2CH3]

d) reducing the compound of Formula V with a suitable reducing agent to obtain 2-Amino-5-hydroxy propiophenone of Formula I; (or)

e) reducing the compound of Formula IV with a suitable reducing agent to obtain a compound of Formula VI and Formula VI

[Structure: PG-O-phenyl(with NH2)-C(=O)-CH2CH3]

f) deprotecting the compound of Formula VI with a suitable deprotecting agent to obtain 2-Amino-5-hydroxy propiophenone of Formula I.

In accordance with another embodiment, the present invention provides a process for preparation of 2-Amino-5-hydroxy propiophenone of Formula I, comprising:
  a) reacting a compound Formula II with a suitable hydroxyl protecting agent to obtain a compound of Formula III; wherein "PG" represents a suitable hydroxyl protecting group,
  b) reacting the compound of Formula III with a suitable nitrating reagent to obtain a compound of Formula IV,
  c) deprotecting the compound of Formula IV with a suitable deprotecting agent to obtain a compound of Formula V, and
  d) reducing the compound of Formula V with a suitable reducing agent to obtain 2-Amino-5-hydroxy propiophenone of Formula I; (or)
  e) reducing the compound of Formula IV with a suitable reducing agent to obtain a compound of Formula VI and
  f) deprotecting the compound of Formula VI with a suitable deprotecting agent to obtain 2-Amino-5-hydroxy propiophenone of Formula I; wherein the "PG" is selected from the group comprising of trichloroethyl formate, methyl formate, ethyl formate, hexyl formate, isobutyl formate, benzyl formate, methoxymethyl, methoxyethoxymethyl, tetrahydropyranyl, tetrahydrofuran, allyl, methoxytrityl, methylthio methyl, benzyl, benzoyl, p-methoxybenzyl, t-butyldimethylsilyl, t-butyldiphenylsilyl, triisopropylsilyl, di-tert-butylsilylene, tetraisopropyldisiloxanylidene, pivaloyl and benzoyl.

In accordance with another embodiment, the present invention provides a process for preparation of 2-Amino-5-hydroxy propiophenone of Formula I, comprising:
  a) reacting a compound of Formula III with a suitable nitrating reagent to obtain a compound of Formula IV, wherein "PG" represents a suitable hydroxyl protecting group,
  b) deprotecting the compound of Formula IV with a suitable deprotecting agent to obtain a compound of Formula V, and
  c) reducing the compound of Formula V with a suitable reducing agent to obtain 2-Amino-5-hydroxy propiophenone of Formula I; (or)
  d) reducing the compound of Formula IV with a suitable reducing agent to obtain a compound of Formula VI and
  e) deprotecting the compound of Formula VI with a suitable deprotecting agent to obtain 2-Amino-5-hydroxy propiophenone of Formula I; wherein the "PG" is selected from the group comprising of trichloroethyl formate, methyl formate, ethyl formate, hexyl formate, isobutyl formate, benzyl formate, methoxymethyl, methoxyethoxymethyl, tetrahydropyranyl, tetrahydrofuran, allyl, methoxytrityl, methylthio methyl, benzyl, benzoyl, p-methoxybenzyl, t-butyldimethylsilyl, t-butyldiphenylsilyl, triisopropylsilyl, di-tert-butylsilylene, tetraisopropyldisiloxanylidene, pivaloyl and benzoyl.

In accordance with another embodiment, the present invention provides a compound of Formula III, Formula III

[Structure: PG-O-phenyl-C(=O)-CH2CH3]

wherein the "PG" represents a suitable hydroxyl protecting group.

In accordance with another embodiment, the present invention provides a compound of Formula III, wherein the "PG" is selected from the group comprising trichloroethyl formate, methyl formate, ethyl formate, hexyl formate, isobutyl formate, benzyl formate, methoxymethyl, methoxyethoxymethyl, tetrahydropyranyl, tetrahydrofuran, allyl, methoxytrityl, methylthiomethyl, benzyl, benzoyl, p-methoxybenzyl, t-butyldimethylsilyl, t-butyldiphenylsilyl, triisopropylsilyl, di-tert-butylsilylene, tetraisopropyldisiloxanylidene, pivaloyl and benzoyl.

In accordance with another embodiment, the present invention provides a compound of Formula III, wherein the "PG" is selected from trichloroethyl formate, ethyl formate or hexyl formate.

In accordance with another embodiment, the present invention provides a compound of Formula IIIa.

Formula IIIa

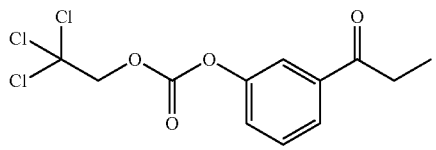

In accordance with another embodiment, the present invention provides a compound of Formula IIIb.

Formula IIIb

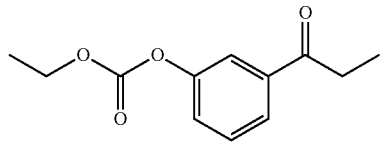

In accordance with another embodiment, the present invention provides a compound of Formula IIIc.

Formula IIIc

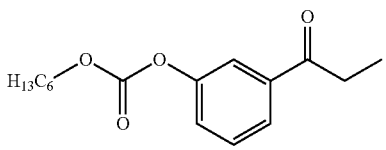

In accordance with another embodiment, the present invention provides a compound of Formula IV:

Formula IV

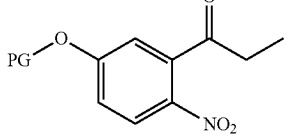

wherein the "PG" represents a suitable hydroxyl protecting group.

In accordance with another embodiment, the present invention provides a compound of Formula IV; wherein the "PG" is selected from the group comprising of trichloroethyl formate, methyl formate, ethyl formate, hexyl formate, isobutyl formate, benzyl formate, methoxymethyl, methoxyethoxymethyl, tetrahydropyranyl, tetrahydrofuran, allyl, methoxytrityl, methylthiomethyl, benzyl, benzoyl, p-methoxybenzyl, t-butyldimethylsilyl, t-butyldiphenylsilyl, triisopropylsilyl, di-tert-butylsilylene, tetraisopropyldisiloxanylidene, pivaloyl and benzoyl.

In accordance with another embodiment, the present invention provides a compound of Formula IV, wherein the "PG" is selected from trichloroethyl formate, ethyl formate or hexyl formate.

In accordance with another embodiment, the present invention provides a process for preparation of compound of Formula IV, comprising; reacting a compound of Formula III with a suitable nitrating reagent to obtain a compound of Formula IV;

Formula III

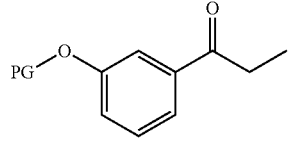

Formula IV

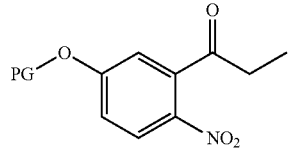

wherein the "PG" is selected from the group comprising of trichloroethyl formate, methyl formate, ethyl formate, hexyl formate, isobutyl formate, benzyl formate, methoxymethyl, methoxyethoxymethyl, tetrahydropyranyl, tetrahydrofuran, allyl, methoxytrityl, methylthiomethyl, benzyl, benzoyl, p-methoxybenzyl, t-butyldimethylsilyl, t-butyldiphenylsilyl, triisopropylsilyl, di-tert-butylsilylene, tetraisopropyldisiloxanylidene, pivaloyl and benzoyl.

In accordance with another embodiment, the present invention provides a compound of Formula IVa.

Formula IVa

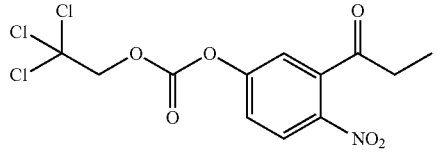

In accordance with another embodiment, the present invention provides a compound of Formula IVb.

Formula IVb

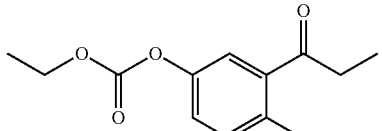

In accordance with another embodiment, the present invention provides a compound of Formula IVc.

Formula IVc

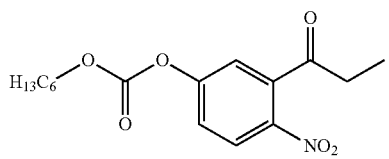

In accordance with another embodiment, the present invention provides a compound of Formula VI.

Formula IV

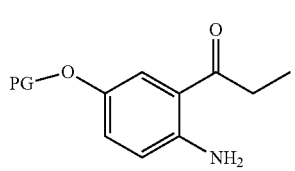

wherein the "PG" represents a suitable hydroxyl protecting group.

In accordance with another embodiment, the present invention provides a compound of Formula VI; wherein the "PG" is selected from the group comprising of trichloroethyl formate, methyl formate, ethyl formate, hexyl formate, isobutyl formate, benzyl formate, methoxymethyl, methoxyethoxymethyl, tetrahydropyranyl, tetrahydrofuran, allyl, methoxytrityl, methylthiomethyl, benzyl, benzoyl, p-methoxybenzyl, t-butyldimethylsilyl, t-butyldiphenylsilyl, triisopropylsilyl, di-tert-butylsilylene, tetraisopropyldisiloxanylidene, pivaloyl and benzoyl.

In accordance with another embodiment, the present invention provides a compound of Formula VI, wherein the "PG" is selected from trichloroethyl formate, ethyl formate or hexyl formate.

In accordance with another embodiment, the present invention provides a process for preparation of compound of Formula VI, comprising reducing a compound of Formula IV with a suitable reducing to obtain a compound of Formula VI; wherein the "PG" is selected from the group comprising of trichloroethyl formate, methyl formate, ethyl formate, hexyl formate, isobutyl formate, benzyl formate, methoxymethyl, methoxyethoxymethyl, tetrahydropyranyl, tetrahydrofuran, allyl, methoxytrityl, methylthiomethyl, benzyl, benzoyl, p-methoxybenzyl, t-butyldimethylsilyl, t-butyldiphenylsilyl, triisopropylsilyl, di-tert-butylsilylene, tetraisopropyldisiloxanylidene, pivaloyl and benzoyl.

In accordance with another embodiment, the present invention provides a process for the preparation of irinotecan, which comprises: preparing a compound of Formula I according to processes described as above and converting the compound of Formula I into 7-Ethyl-10-hydroxycamptothecin (SN-38) and subsequently to Irinotecan.

DETAILED DESCRIPTION OF THE INVENTION

The present invention provides a process for the preparation of 2-Amino-5-hydroxy propiophenone of Formula I, an intermediate compound useful in the preparation of 7-Ethyl-10-hydroxycamptothecin (SN-38).

In accordance with one embodiment, the present invention provides a process for preparation of 2-Amino-5-hydroxy propiophenone of Formula I:

Formula I

comprising:
a) reacting a compound of Formula III wherein "PG" is a suitable hydroxyl protecting group, with a suitable nitrating reagent to obtain a compound of Formula IV, and Formula III

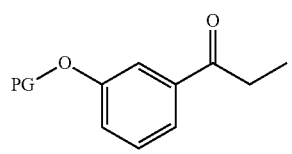

Formula IV

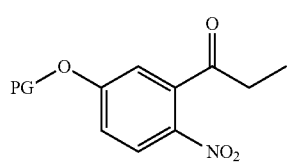

b) converting the compound of Formula IV in to 2-Amino-5-hydroxy propiophenone of Formula I.

In accordance with another embodiment, the present invention provides a process for preparation of 2-Amino-5-hydroxy propiophenone of Formula I:

Formula I

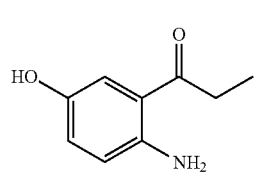

comprising:
a) reacting a compound Formula II with a suitable hydroxyl protecting agent to obtain a compound of Formula III; wherein "PG" represents a suitable hydroxyl protecting group, Formula II

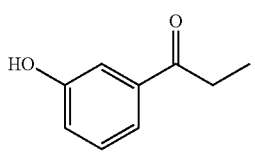

Formula III

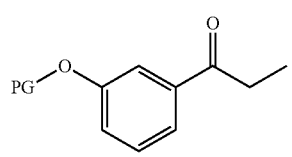

b) reacting the compound of Formula III with a suitable nitrating reagent to obtain a compound of Formula IV, and

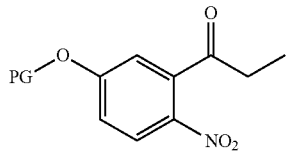

Formula IV d) converting the compound of Formula IV in to 2-Amino-5-hydroxy propiophenone of Formula I.

In another embodiment, the present invention provides a process for preparation of 2-Amino-5-hydroxy propiophenone of Formula I:

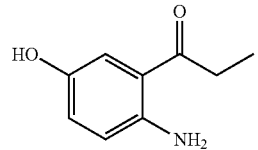

Formula I comprising:

a) reacting a compound Formula II with a suitable hydroxyl protecting agent to obtain a compound of Formula III; wherein "PG" represents a suitable hydroxyl protecting group,

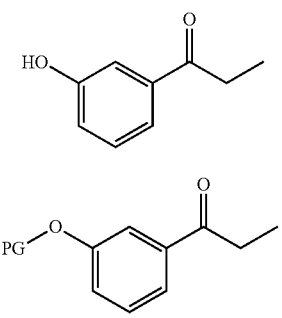

Formula II

Formula III b) reacting the compound of Formula III with a suitable nitrating reagent to obtain a compound of Formula IV,

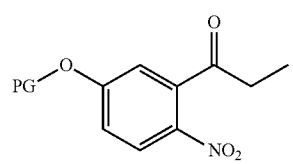

Formula V c) deprotecting the compound of Formula IV with a suitable deprotecting agent to obtain a compound of Formula V, and

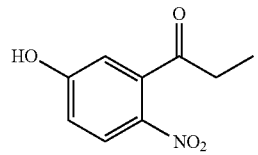

Formula V d) reducing the compound of Formula V with a suitable reducing agent to obtain 2-Amino-5-hydroxy propiophenone of Formula I; (or)

e) reducing the compound of Formula IV with a suitable reducing agent to obtain a compound of Formula VI and

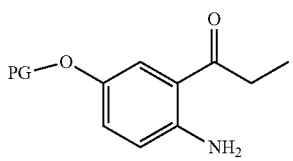

Formula VI f) deprotecting the compound of Formula VI with a suitable deprotecting agent to obtain 2-Amino-5-hydroxy propiophenone of Formula I.

The starting materials, a compound of Formula II is well known in the art and it can be produced by methods known in the art recognized by the organic chemist of ordinary skill in the art.

The present invention relates to a process for preparation of 2-Amino-5-hydroxy propiophenone of Formula I, by mainly involving regioselective nitration by creating steric hindrance on 3'-hydroxy propiophenone through protecting the hydroxy group, which is advantageously avoids the formation of regio isomers/positional isomers, thereby making the process free from tedious column purification and/or crystallization steps, which process steps are considered in the prior art to separate un-wanted regio isomers/positional isomers. The regioselective process of the present invention is more suitable for commercial applications with higher regio selectivity and obviates the problems associated with the reported processes.

Protection of Hydroxy Group:

The step a) of forgoing process involves hydroxy protection of a compound Formula II with a suitable protecting group forming agent in presence of a base and in a solvent to obtain a compound of Formula III; wherein "PG" is a suitable protecting group.

The suitable hydroxyl protecting group includes but is not limited to trichloroethyl formate, methyl formate, ethyl formate, hexyl formate, isobutyl formate, benzyl formate, methoxymethyl, methoxyethoxymethyl, tetrahydropyranyl, tetrahydrofuran, allyl, methoxytrityl, methylthiomethyl, benzyl, benzoyl, p-methoxybenzyl, t-butyldimethylsilyl, t-butyldiphenylsilyl, triisopropylsilyl, di-tert-butylsilylene, tetraisopropyldisiloxanylidene, pivaloyl and benzoyl. Other hydroxy protecting groups are well known in the art can also be considered as hydroxyl protecting groups of the invention, specifically described in detail in Protecting Groups in Organic Synthesis, Theodora W. Greene and Peter G. M. Wuts, 3$^{rd}$ Edition, 1999, published by John Wiley and Son, Inc; preferably the protecting group is trichloroethyl formate, ethyl formate and hexyl formate.

The suitable hydroxyl protecting group forming agent includes but not limited to trichloroethyl chloroformate, methyl chloroformate, ethyl chloroformate, hexyl chloroformate, isobutyl chloroformate, benzylchloroformate, methoxymethylchloride, methoxyethoxy methylchloride, tetrahydropyranyl ether, allyl bromide, methoxytrityl chloride, methylthiomethyl chloride, benzyl bromide, benzoyl bromide, p-methoxybenzyl chloride, t-butyldimethylsilyl chloride, t-butyldiphenylsilyl chloride, triisopropylsilyl chloride, di-tert-butylsilylene chloride, tetraisopropyl disiloxanylidene chloride, pivaloyl chloride and benzoyl chloride; preferably trichloroethyl chloroformate, ethyl chloroformate or hexyl chloroformate.

The suitable base used herein step a) is selected from either inorganic base or organic base; further, the suitable inorganic base is selected from, but is not limited to, alkali metal hydroxides such as sodium hydroxide, potassium hydroxide and the like; alkali metal hydrides such as sodium hydride, potassium hydride and the like; alkali metal amides such as sodium amide, potassium amide, lithium amide and the like; alkali metal alkoxides such as sodium methoxide, sodium ethoxide, sodium t-butoxide, potassium t-butoxide and the like; alkali metal carbonates such as sodium carbonate, potassium carbonate, cesium carbonate and the like; alkali metal bicarbonates such as sodium bicarbonate, potassium bicarbonate and the like; phosphates such as sodium phosphate, trisodium phosphate, potassium phosphate, tripotassium phosphate and the like; ammonium carbonate; and the organic base is selected from, but is not limited to, triethylamine, tri-n-propylamine, tri-n-butylamine, methyldibutylamine, diisopropylamine, diisopropylethylamine, dicyclohexylamine, methyl dicyclohexylamine, ethyldiisopropyl amine, N,N-diethyldicyclohexylamine, pyridine, dimethylamino-4-pyridine, N-methyl piperidine, N-ethylpiperidine, N-ethylpiperidine, N-butylpiperidine, 1,2-dimethyl piperidine and the like; or mixtures thereof; preferably sodium hydroxide, sodium hydride, sodium amide, potassium t-butoxide or cesium carbonate; more preferably sodium hydroxide.

The suitable solvent used herein in step a) is selected from, but is not limited to ketones include, but are not limited to acetone, methyl ethyl ketone, methyl isobutyl ketone, diethyl ketone and the like; nitriles include, but are not limited to acetonitrile, propionitrile and the like; ethers include, but are not limited to diethyl ether, tetrahydrofuran, methyl tetrahydrofuran, 1,4-dioxane and the like; polar aprotic solvent include, but are not limited to dimethylacetamide, dimethylformamide, dimethylsulfoxide, N-methylpyrrolidone and the like; halogenated solvents include, but are not limited to methylene chloride, ethylene chloride, chloroform and the like; aromatic hydrocarbons include, but are not limited to toluene, xylene and the like; water or mixtures thereof; preferably the suitable solvent is acetonitrile, tetrahydrofuran, dimethylformamide, methylene chloride, water or mixtures thereof; more preferably methylene chloride, water or mixtures thereof.

The reaction of a compound Formula II with a suitable hydroxyl protecting group is carried out at a temperature of about −10° C. to reflux temperature; preferably at a temperature of about 0° C. to about 80° C.

After completion of the protection reaction, the resultant compound of Formula III may be isolated as a solid form for the conversion of subsequent steps or may be proceed further without isolating the same. If isolation involves, the isolation can be carried out by either direct filtration of the precipitated solid or by extracting the reaction mass with a suitable water immiscible organic solvent; preferably ethyl acetate, methylene chloride and the like; more preferably methylene chloride. Then the product containing organic layer may be separated and the compound of Formula III can be isolated by either precipitation, evaporation and the resultant product may optionally be further dried.

In another embodiment, the compound of Formula III is specifically represented as a compound of Formula IIIa, Formula IIIb or Formula IIIc.

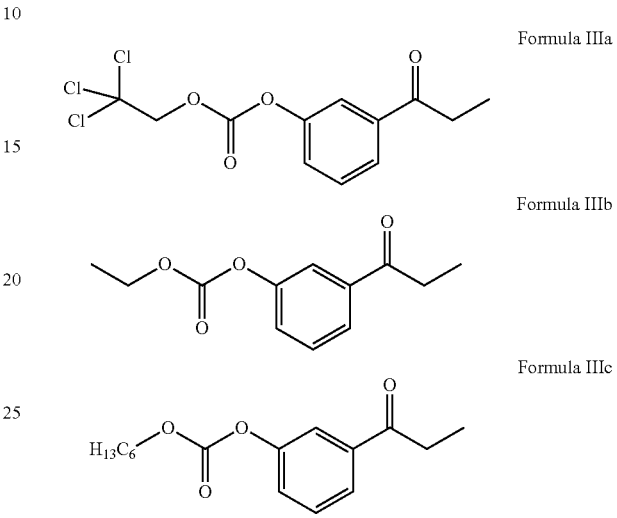

Nitration Reaction:

To date all reported nitration processes in the art involves formation of unwanted regio isomers/positional isomers in the nitration reaction by substitution of nitro group at both ortho and para positions instead of same reaction at only para position. This is due to the presence of free hydroxyl group and as a result lack of steric hindrance at both ortho and para positions possibility of nitration at both the positions is highly favorable. Nitration at multiple positions instead of required only at para position creates unnecessary burden to the commercial scale process as regio isomeric impurities formed are difficult to remove from the required product by the normal purification techniques due to low polarity difference of the regio isomers. Therefore requires multiple column purifications and even then no guarantee to getting the highly pure compound as required for the pharmaceutical use.

To overcome the difficulties associated with the art, the inventors of the present invention have surprisingly found that creating the steric hindrance by protecting the neighboring free hydroxyl group on the aryl ring with a suitable protecting group that avoids the nitration at unwanted ortho position and favors to only required para position therefore formation of unwanted regio isomers are greatly reduced as a result making the current process free from tedious column purification and/or multiple crystallization steps to separate un-wanted isomers and making the process higher yields and pure.

The nitration step b) of the forgoing process involves reaction of the compound of Formula III with a suitable nitrating reagent to obtain a compound of Formula IV; wherein "PG" is a suitable protecting group.

The suitable nitrating reagent may be selected from the group comprising nitrating mixture (a mixture of nitric acid and sulfuric acid), sodium nitrate, potassium nitrate, calcium nitrate, cupric nitrate and the like and mixtures thereof; preferably nitrating mixture or potassium nitrate.

The reaction of Formula III with a suitable nitrating reagent may be advantageously carried out in a suitable solvent. The suitable solvent includes but is not limited to halogenated hydrocarbons, aromatic hydrocarbons, amides, nitriles, acid and mixtures thereof. The halogenated hydrocarbons include, but are not limited to methylene chloride, ethylene chloride, chloroform and the like; aromatic hydrocarbons include, but are not limited to toluene, xylene and the like; amides include, but are not limited to dimethyl formamide, dimethyl acetamide, dimethyl sulfoxide, N-methyl pyrrolidinone and the like; nitriles include, but are not limited to acetonitrile, propionitrile and the like; preferably methylene chloride.

The nitration step may be optionally carried out in presence of an acid selected from the group comprising hydrochloric acid, hydrobromic acid, sulfuric acid, perchloric acid, phosphoric acid, acetic acid, acetic anhydride, trifluoro acetic acid, trichloro acetic acid, methane sulfonic acid and the like and mixtures thereof, preferably sulfuric acid.

The reaction of compound of Formula III with a suitable nitrating reagent is carried out at a temperature of about −25° C. to about reflux temperature; Preferably the reaction is carried out at about −15° C. to about 15° C.

The resultant compound of Formula IV may be isolated as a solid form for the conversion of subsequent steps or may be proceed further without isolating the same. If isolation involves, the isolation can be carried out by either direct filtration of the precipitated solid or by extracting the reaction mass with a suitable water immiscible organic solvent; preferably ethyl acetate, methylene chloride and the like; more preferably methylene chloride. Then the product containing organic layer may be separated and the compound of Formula IV can be isolated by either precipitation, evaporation and the resultant product may optionally be further dried.

In another embodiment, the compound of Formula IV is specifically represented as a compound of Formula IVa, Formula IVb or Formula IVc.

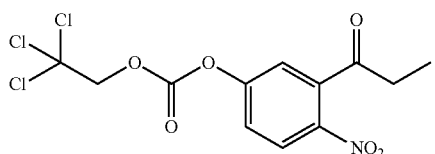

Formula IVa

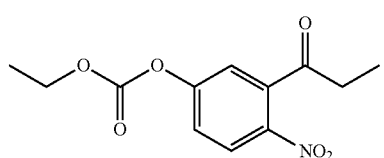

Formula IVb

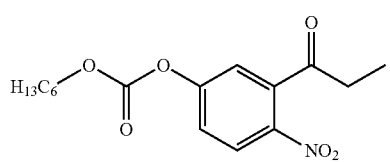

Formula IVc

In accordance with another embodiment, the present invention provides a process for preparation of 2-Amino-5-hydroxy propiophenone of Formula I, comprising: converting the above obtained compound of Formula IV in to 2-Amino-5-hydroxy propiophenone of Formula I by either involving deprotecting the compound of Formula IV with a suitable deprotecting agent to obtain a compound of Formula V and then reducing the compound of Formula V with a suitable reducing agent to obtain 2-Amino-5-hydroxy propiophenone of Formula I, (or) reducing first the compound of Formula IV with a suitable reducing agent to obtain a compound of Formula VI and then deprotecting the compound of Formula VI with a suitable deprotecting agent to obtain 2-Amino-5-hydroxy propiophenone of Formula I.

Deprotection Reaction:

The forgoing process of deprotection step involves deprotection of hydroxy protection group of compound of Formula IV or compound of Formula VI in presence of a suitable deprotecting agent at a temperature of about 0° C. to about reflux temperature; preferably the reaction is carried out at about 25° C. to about 50° C.

The suitable deprotecting agent used herein for deprotecting either compound of Formula IV or compound of Formula VI may be selected from a suitable base or a suitable acid. The suitable base includes, but is not limited to inorganic bases selected from alkali metal hydroxides such as lithium hydroxide, sodium hydroxide, potassium hydroxide and the like; alkali metal alkoxides such as sodium methoxide, sodium ethoxide, sodium tert-butoxide, potassium tert-butoxide and the like; alkali metal carbonates such as sodium carbonate, potassium carbonate, cesium carbonate and the like; alkali metal bicarbonates such as sodium bicarbonate, potassium bicarbonate and the like; and organic bases selected from the group consisting of triethylamine, isopropyl ethylamine, diisopropyl amine, diisopropyl ethylamine, N-methyl morpholine, piperidine, pyridine and the like and mixtures thereof. The suitable acid includes, but is not limited to hydrochloric acid, hydrobromic acid, boron tribromide, trimethylsilyl iodide, zinc bromide, titanium(IV) chloride, 2,3-dichloro-5,6-dicyanobenzoquinone and the like and mixture thereof, preferably sodium hydroxide, potassium carbonate, hydrochloric acid and mixture thereof; more preferably potassium carbonate.

The deprotection reaction is advantageously carried out in a suitable solvent. The suitable solvent includes but is not limited to alcohols, halogenated hydrocarbons, amides, nitriles, acids and mixtures thereof. The alcohols include, but are not limited to methanol, ethanol, isopropanol, n-butanol and the like; halogenated hydrocarbons include, but are not limited to methylene chloride, ethylene chloride, chloroform and the like; amides include, but are not limited to dimethyl formamide, dimethyl acetamide, dimethyl sulfoxide, N-methyl pyrrolidinone and the like; nitriles include, but are not limited to acetonitrile, propionitrile and the like; acids include, but are not limited to formic acid, acetic acid and the like and mixtures thereof; preferably methanol, ethanol, dimethyl formamide and mixtures thereof, more preferably methanol.

After completion of the deprotection reaction, the resultant compound of Formula V or Formula VI may be isolated as a solid form for the conversion of subsequent steps or may be proceed further without isolating the same. If isolation involves, the isolation can be carried out by either direct filtration of the precipitated solid or by extracting the reaction mass with a suitable water immiscible organic solvent; preferably ethyl acetate, methylene chloride and the like; preferably methylene chloride. Then the product containing organic layer may be separated and the compound of Formula V or Formula VI can be isolated by either precipitation, evaporation and the resultant product may optionally be further dried.

Nitro Reduction:

The forgoing process of nitro reduction step involves reduction of compound of Formula IV or compound of Formula V in presence of a suitable reducing agent at a temperature of about 25° C. to about reflux temperature; preferably the reaction is carried out at about 25° C. to about 80° C.

The suitable reducing agent for reduction of nitro group is selected from the group comprising of Iron in HCl, Iron/$NH_4Cl$, $SnCl_2$, Sodium dithionite, Sodium hydrosulfite, Tin (II) chloride, Titanium (III) chloride, Zinc/$NH_4Cl$, Zn/hydrazine hydrate, Iron/hydrazine hydrate, raney nickel and the like and mixtures thereof. The reduction step can be carried out in combination with hydrogen gas; preferably Sodium dithionite, Iron/$NH_4Cl$ or Raney nickel/Hydrogen gas; more preferably sodium dithionite.

The reduction reaction is advantageously carried out in a suitable solvent. The suitable solvent includes but is not limited to alcohols, halogenated hydrocarbons, nitriles, water and mixtures thereof. The alcohols include, but are not limited to methanol, ethanol, isopropanol, n-butanol and the like; halogenated hydrocarbons include, but are not limited to methylene chloride, ethylene chloride and the like; nitriles include, but are not limited to acetonitrile, propionitrile and the like; water and mixtures thereof; preferably methanol, ethanol, water and mixtures thereof; more preferably water.

After completion of the reduction reaction, the resultant compound of Formula I may be isolated as a solid by direct filtration of reaction mass or may be isolated by extracting the reaction mass with a suitable water immiscible organic solvent; preferably ethyl acetate, methylene chloride and the like. Then the product containing organic layer may be separated and the compound of Formula I can be isolated by either precipitation, evaporation and the resultant product may optionally be further dried.

The present invention provides 2-Amino-5-hydroxy propiophenone of Formula I, obtained by the process described herein, having a purity of at least about 95%, as measured by HPLC, preferably at least about 97% as measured by HPLC, and more preferably at least about 99%, as measured by HPLC; and less than 5% of other regio isomer of Formula I' and/or Formula I", preferably less than 2% as measured by HPLC.

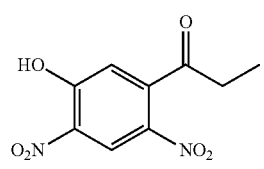

Formula I'

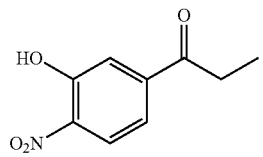

Formula I"

The 'Aurore reference discloses nitration reaction at unprotected hydroxy compound, results a compound of Formula IV contains about 60% of regio isomeric impurities of Formula I' and I". In contrast, the process herein described, arrives at a compound of Formula IV, which may be involved protection at hydroxyl group to improve the selectivity of the reaction accordingly compound of Formula IV obtained with a purity of more than about 95% and considerably limit the formation of unwanted regio isomeric impurities of Formula I' and I" to less than about 5% therefore cumbersome column purifications and/or multiple crystallizations are avoided.

Comparative preparation of compound of Formula IV using the 'Aurore process yielded the compound of Formula IV that had substantially higher level of regio isomeric impurities of Formula I' and I" than the present process. The results obtained from the Aurore's process and the present process are summarized in Table I, as shown below under Examples section where values are reported as weight percent (w/w %) as determined by HPLC.

In another embodiment, the present invention provides a compound of Formula III,

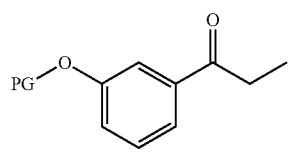

Formula III wherein the "PG" represents a suitable hydroxyl protecting group.

In another embodiment, the present invention provides a compound of Formula III,

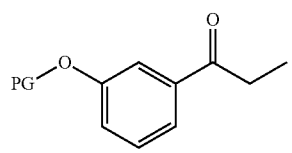

Formula III wherein the "PG" is selected from the group comprising of trichloroethyl formate, methyl formate, ethyl formate, hexyl formate, isobutyl formate, benzyl formate, methoxymethyl, methoxyethoxymethyl, tetrahydropyranyl, tetrahydrofuran, allyl, methoxytrityl, methylthio methyl, benzyl, benzoyl, p-methoxybenzyl, t-butyldimethylsilyl, t-butyldiphenylsilyl, triisopropylsilyl, di-tert-butylsilylene, tetraisopropyldisiloxanylidene, pivaloyl and benzoyl.

In accordance with another embodiment, the present invention provides a compound of Formula III, wherein the "PG" is selected from trichloroethyl formate, ethyl formate or hexyl formate.

In another embodiment, the present invention provides a compound of Formula IIIa.

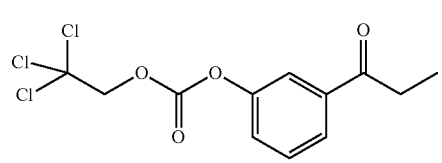

Formula IIIa

In another embodiment, the present invention provides a compound of Formula IIIb.

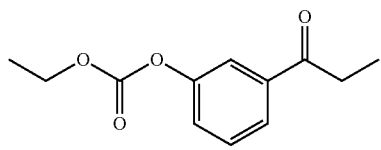
Formula IIIb

In another embodiment, the present invention provides a compound of Formula IIIc.

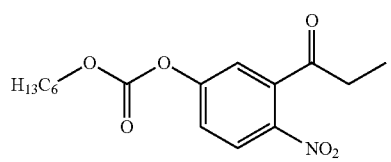
Formula IIIc

In another embodiment, the present invention provides a compound of Formula IV:

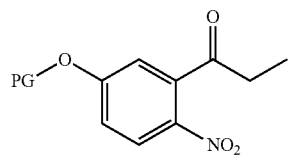
Formula IV wherein the "PG" represents a suitable hydroxyl protecting group.

In another embodiment, the present invention provides a compound of Formula IV.

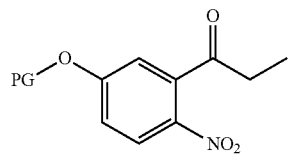
Formula IV wherein the "PG" is selected from the group comprising of trichloroethyl formate, methyl formate, ethyl formate, hexyl formate, isobutyl formate, benzyl formate, methoxymethyl, methoxyethoxymethyl, tetrahydropyranyl, tetrahydrofuran, allyl, methoxytrityl, methylthio methyl, benzyl, benzoyl, p-methoxybenzyl, t-butyldimethylsilyl, t-butyldiphenylsilyl, triisopropylsilyl, di-tert-butylsilylene, tetraisopropyldisiloxanylidene, pivaloyl and benzoyl.

In another embodiment, the present invention provides a compound of Formula IV, wherein the "PG" is selected from trichloroethyl formate, ethyl formate or hexyl formate.

In another embodiment, the present invention provides a compound of Formula IVa.

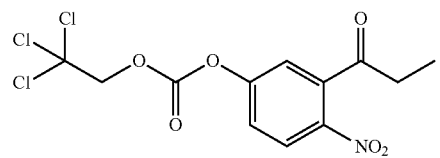
Formula IVa

In another embodiment, the present invention provides a compound of Formula IVb.

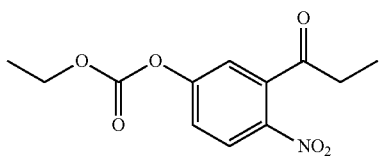
Formula IVb

In another embodiment, the present invention provides a compound of Formula IVc.

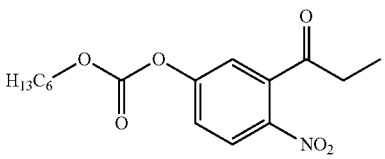
Formula IVc

In another embodiment, the present invention provides a compound of Formula VI.

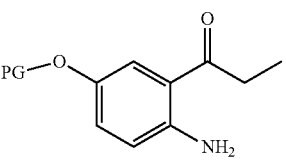
Formula VI wherein the "PG" represents a suitable hydroxyl protecting group.

In another embodiment, the present invention provides a compound of Formula VI.

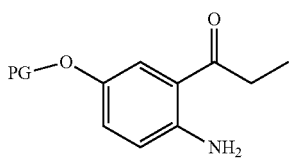
Formula VI wherein the "PG" is selected from the group comprising of trichloroethyl formate, methyl formate, ethyl formate, hexyl formate, isobutyl formate, benzyl formate, methoxymethyl, methoxyethoxymethyl, tetrahydropyranyl, tetrahydrofuran, allyl, methoxytrityl, methylthio methyl, benzyl, benzoyl, p-methoxybenzyl, t-butyldimethylsilyl, t-butyldiphenylsilyl, triisopropylsilyl, di-tert-butylsilylene, tetraisopropyldisiloxanylidene, pivaloyl and benzoyl.

In another embodiment, the present invention provides a compound of Formula VI, wherein the "PG" is selected from trichloroethyl formate, ethyl formate or hexyl formate.

In accordance with another embodiment, the present invention provides a process for the preparation of irinotecan, which comprises: preparing a compound of Formula I according to processes described as above and converting the compound of Formula I to 7-Ethyl-10-hydroxycamptothecin (SN-38) and subsequently to Irinotecan.

The compound of Formula I prepared by the process of the present invention can be used as an intermediate in the preparation of 7-Ethyl-10-hydroxycamptothecin (SN-38) and subsequently converting it in to Irinotecan, by the methods known in the art recognized by the organic chemist of ordinary skill in the art.

The present invention provides 2-Amino-5-hydroxy propiophenone of Formula I and its intermediates, obtained by the above process, as analyzed using the high performance liquid chromatography ("HPLC") with the conditions described below:

| Column | Hypersil BDS C18 |
|---|---|
| Column temperature | 30° C. |
| Flow rate | 1.0 mL/min |
| Injection volume | 10 µL |
| Diluent | Water: Acetonitrile |
| Wavelength | 210 nm |
| Mobile phase | |
| Mobile phase A | 0.01 KH$_2$PO$_4$ |
| Mobile phase B | Acetonitrile |
| Elution | Gradient |

| Time (minutes) | Mobile phase A (%) | Mobile phase B (%) |
|---|---|---|
| 0 | 65 | 35 |
| 5 | 65 | 35 |
| 20 | 20 | 80 |
| 30 | 20 | 80 |
| 35 | 65 | 35 |

EXAMPLES

The present invention is further illustrated by the following examples, which are provided by way of illustration only and should not be construed to limit the scope of the invention.

Example 1

Preparation of Compound of Formula IIIa (PG: 2,2,2-trichloroethyl Chloroformate)

To a 2 lit round bottom flask fitted with a mechanical stirrer, thermometer was charged water (700 ml) and 3-hydroxy propiophenone (140 g) at 25° C. to 30° C. Reaction mass was cooled to 0° C. to 10° C. and was added NaOH solution (39.1 g of NaOH dissolved in 140 ml of water). Stirred the reaction mass for 10 min at same temperature and added 2,2,2-trichloroethyl chloroformate (237.3 g) to the reaction mass while maintaining the temperature below 10° C. Reaction mass was stirred for 2 hr at 0° C. to 10° C. After completion of the reaction, filtered the solid and was washed the cake with hexane (300 ml) and dried the wet material under vacuum to get 224 g of Formula III. $^1$H NMR (DMSO): δ=1.09 (t, 3H), 3.07 (q, 2H), 5.08 (s, 2H) 7.57-7.96 (m, 4H); Purity by HPLC: 99.5%.

Example 2

Preparation of compound of Formula IVa (PG: 2,2,2-trichloroethyl Chloroformate)

To a 1 lit round bottom flask fitted with a mechanical stirrer, thermometer was charged compound of Formula IIIa from Example-1 (50 g) and methylene chloride (500 ml) at 25° C. to 30° C. To the reaction mass was added anhydrous sodium sulphate (25 g) at same temperature. Reaction mass was cooled to 5° C. to 10° C. and was added sulphuric acid (125 ml). Reaction mass was cool to −1° C. and was added potassium nitrate (38.7 g) portion-wise at same temperature. Reaction mass was stirred for 60 min at 5-10° C. After completion of the reaction, poured the reaction mass into pre cooled water (1000 ml). Separated the organic layer and aqueous layer was extracted methylene chloride (400 ml). Then the combined organic layer was washed with 2M NaOH solution (500 ml) and 10% sodium chloride solution (500 ml). Combined organic layer was completely distilled under vacuum to afford 47.3 g of Formula IV. $^1$H NMR (DMSO): δ=1.12 (t, 3H), 2.91 (q, 2H), 5.10 (s, 2H) 7.72 (d, J=2.4 Hz, 1H), 7.77 (dd, 1H), 8.29 (d, J=9 Hz, 1H); Purity by HPLC: 98%.

Example 3

Preparation of Compound of Formula V

To a 1 lit round bottom flask fitted with a mechanical stirrer, thermometer was charged compound of Formula IVa (46 g) from Example-2, potassium carbonate (25 g) and methanol (500 ml) at 25° C. to 30° C. and stirred the reaction mass for 60 min at same temperature. After completion of the reaction, filter the salts and to the filtrate charged water (500 ml). Aqueous layer was washed with methylene chloride (250 ml). pH of the mass was adjusted to 3.5 using hydrochloric acid solution. Then the reaction mass was extracted with methylene chloride (1×500 ml and 1×250 ml). Combined organic layer was washed with water (250 ml). Organic layer was distilled completely under vacuum and stripped out the residue with hexane (100 ml). Charged toluene (50 ml) to the crude material and stirred for 30 min at 25° to 30° C. Filtered the solid to afford 20 g of Formula V. $^1$H NMR (DMSO): 5=1.10 (t, 3H), 2.77 (q, 2H), 6.81 (d, J=2.4 Hz, 1H), 6.99 (dd, 1H), 8.10 (d, J=9 Hz, 1H) 11.37 (brs, 1H); Purity by HPLC: 97.5%.

Example 4

Preparation of Compound of Formula I

To a 500 ml round bottom flask fitted with a mechanical stirrer, thermometer was charged water (125 ml), sodium dithionite (17.8 g) and sodium carbonate (8.7 g) at 25° C. to 30° C. and stirred for 10 min at same temperature. Reaction mass was cool to 0° C. to 5° C. and was added solution of compound of Formula V (5 g dissolved in 10 ml of methanol) at same temperature. Reaction mass was allowed to 25° C. to 30° C. and stirred for 1 h. Filtered the solid and washed with water to afford 3.6 g of 2-Amino 5-hydroxy propipheneone of Formula I. $^1$H NMR (DMSO): 5=1.05 (t, 3H), 2.87 (q, 2H), 6.16 (s, 2H), 6.45 (d, 1H), 6.81 (dd, 1H), 7.11 (d, J=9 Hz, 1H), 8.65 (s, 1H); Purity by HPLC: 97.5%.

Example 5

Preparation of Compound of Formula IIIb (PG: Ethyl Chloroformate)

To a 500 ml round bottom flask fitted with a mechanical stirrer, thermometer was charged water (100 ml) and 3-hydroxy propiophenone (20 g) at 25° C. to 30° C. Reaction mass was cooled to 0° C. to 10° C. and was added NaOH solution (9.6 g of NaOH dissolved in 20 ml of water). Stirred the reaction mass for 10 min at same temperature and was added ethyl chloroformate (17.4 g) to the reaction mass while maintaining the temperature below 10° C. After completion of the reaction, reaction mass was extracted with methylene chloride (150 ml) and organic layer was washed with 10% NaOH (100 ml). The resulting organic layer was distilled completely under vacuum at below 50° C. Charged 500 ml of hexane, kept the mass for overnight at 2-8° C. Filtered the solid and was washed the cake with chilled hexane (50 ml) and dried the wet material under vacuum to get 15.5 g of ethyl carbonate of 3-hydroxy propiophenone.

Example 6

Preparation of Compound of Formula IVb (PG: Ethyl Chloroformate)

To a 250 ml round bottom flask fitted with a mechanical stirrer, thermometer was charged compound of Formula IIIb from Example-5 (5 g) and methylene chloride (50 ml) at 25° C. to 30° C. under nitrogen atmosphere. To the reaction mass was added anhydrous sodium sulphate (2.5 g) at same temperature. Reaction mass was cooled to 5° C. to 10° C. and was added sulphuric acid (18.3 ml) and potassium nitrate (5.7 g) portion-wise at below 10° C. Reaction mass was stirred for 60 min at 0-10° C. After completion of the reaction, poured the reaction mass into pre cooled water (200 ml). Separated the organic layer and aqueous layer was extracted methylene chloride (50 ml). Then the combined organic layer was washed with 2M NaOH solution (100 ml) and 10% sodium chloride solution (100 ml). Combined organic layer was completely distilled under vacuum to afford 2.4 g of Formula IVb.

Example 7

Preparation of Compound of Formula V

To a 100 ml round bottom flask fitted with a mechanical stirrer, thermometer was charged compound of Formula IVb (2 g) from Example-6, potassium carbonate (1 g) and methanol (10 ml) at 25° C. to 30° C. and stirred the reaction mass for 60 min at same temperature. After completion of the reaction, filter the salts and to the filtrate charged water (50 ml). Aqueous layer was washed with methylene chloride (50 ml). pH of the mass was adjusted to 1.2 using hydrochloric acid solution. Then the reaction mass was extracted with methylene chloride (3×50 ml). Organic layer was distilled completely under vacuum to afford 1.4 g of Formula V.

Example 8

Preparation of Compound of Formula IIIc (PG: Hexyl Chloroformate)

To a 500 ml round bottom flask fitted with a mechanical stirrer, thermometer was charged water (120 ml) and 3-hydroxy propiophenone (20 g) at 25° C. to 30° C. Reaction mass was cooled to 0° C. to 10° C. and was added NaOH solution (9.6 g of NaOH dissolved in 20 ml of water). Stirred the reaction mass for 10 min at same temperature and was added hexyl chloroformate (26.3 g) to the reaction mass while maintaining the temperature below 10° C. After completion of the reaction, reaction mass was extracted with methylene chloride (150 ml) and organic layer was washed with 10% NaOH (100 ml). The resulting organic layer was distilled completely under vacuum at below 50° C. to get 34.8 g of hexyl carbonate of 3-hydroxy propiophenone.

Example 9

Preparation of Compound of Formula IVc (PG: Hexyl Chloroformate)

To a 250 ml round bottom flask fitted with a mechanical stirrer, thermometer was charged compound of Formula IIIc from Example-8 (5 g) and methylene chloride (50 ml) at 25° C. to 30° C. under nitrogen atmosphere. To the reaction mass was added anhydrous sodium sulphate (5 g) at same temperature. Reaction mass was cooled to 5° C. to 10° C. and was added sulphuric acid (15 ml) and potassium nitrate (4.6 g) portion-wise at below 10° C. Reaction mass was stirred for 2 hr at 5-10° C. After completion of the reaction, poured the reaction mass into pre cooled water (200 ml). Separated the organic layer and aqueous layer was extracted methylene chloride (100 ml). Then the combined organic layer was washed with 2M NaOH solution (100 ml) and 10% sodium chloride solution (100 ml). Combined organic layer was completely distilled under vacuum to afford 5.3 g of Formula IV.

Example 10

Preparation of Compound of Formula V

To a 100 ml round bottom flask fitted with a mechanical stirrer, thermometer was charged compound of Formula IVc (5 g) from Example-9, potassium carbonate (3 g) and methanol (50 ml) at 25° C. to 30° C. and stirred the reaction mass for 60 min at same temperature. After completion of the reaction, filter the salts and to the filtrate charged water (50 ml). Aqueous layer was washed with methylene chloride (50 ml). pH of the mass was adjusted to 1.5 using hydrochloric acid solution. Then the reaction mass was extracted with methylene chloride (3×50 ml). Organic layer was distilled completely under vacuum to afford 1.2 g of Formula V.

Example 11

Preparation of Compound of Formula I (PG: 2,2,2-trichloroethyl Chloroformate)

To a 2 lit round bottom flask fitted with a mechanical stirrer, thermometer was charged sodium hydroxide (41.5 g), water (600 mL) and 3-hydroxy propiophenone (120 g) at 25° C. to 30° C. and allowed to stir for 10-15 min at same temperature. To the reaction mass was charged methylene dichloride (480 mL) and allowed to cool to 5-15° C., charged tetrabutyl ammonium bromide (0.6 g) and 2,2,2-trichloroethyl chloroformate (203 g) at 5-15° C. and allowed to stir for 30-40 min at same temperature. After completion of the reaction, separated the organic and aqueous layers and the organic layer was washed with water (2×240 mL) and with sodium chloride solution (24 g dissolved in 240 mL water). Organic layer was separated and concentrated under vacuum at below 40° C. and the solid Formula IIIa was isolated by heptane slurry filtrations.

To a 2 lit round bottom flask fitted with a mechanical stirrer, thermometer was charged the above obtained wet solid (Formula IIIa) and methylene dichloride (672 mL) at 25-30° C. and the reaction mass was allowed to cool to −20 to −25° C. To the reaction mass was added sulphuric acid (389.8 mL) and fuming nitric acid (130 g) at −20 to −25° C. for 30 min. After completion of the reaction, separated the sulphuric acid layer and reaction mass was allowed to 25-30° C. Reaction mass was washed with water (672 mL) and the organic layer was concentrated under vacuum at below 45° C. to obtain Formula IVa.

To a 2 lit round bottom flask fitted with a mechanical stirrer, thermometer was charged the above obtained wet solid (Formula IVa) and methanol (448 mL) at 25-30° C. and stir for 15-30 min at same temperature. To the reaction mass was added potassium carbonate (47.5 g) and stir for 1 hr at 25-30° C. Reaction mass was added to a separately prepared solution of sodium carbonate (182.3 g) and sodium dithionate (357 g) in water (5.6 lit) at 5° C. and allowed to stir for 1 hr at 25-30° C. Precipitated solids were filtered and washed with water (224 mL). The wet solid was dissolved in ethyl acetate (2.6 lit) at 25-30° C. and washed with water (2×560 mL). Organic layer was separated and concentrated completely under vacuum at below 45° C. to obtain title compound and dried under vacuum at 75° C. for 7-8 hrs to afford 57.6 g of title compound. Purity HPLC: 99.9%.

The following comparative examples is carried out by following the teaching of Aurore et al. in *Bioorganic & Medicinal Chemistry Letters* Volume 14, Issue 9, Pages 2363-2365, 2004.

Comparative Example

Preparation of Compound of Formula V from 3'-hydroxy propiophenone

To a 500 ml round bottom flask fitted with a mechanical stirrer, thermometer was charged acetic acid (400 ml) at 25-35° C. and reaction mass heated to 65-70° C. To the reaction mass was charged 65-75% nitric acid (50 ml) at same temperature. After completion of the reaction, cool the reaction mass to 25-35° C. Reaction mass was slowly added to chilled water and extracted with ethyl acetate (2×800 ml). Combined organic layer was distilled under vacuum at below 50° C. to get crude compound. The obtained crude was purified by silica gel column purification using eluent ethyl acetate/hexene. Pure fractions are concentrated under vacuum at below 50° C. to obtain 41 gr of title compound.

TABLE 1

|  | Formula V | Formula I' | Formula I" |
|---|---|---|---|
| Comparative Example | 30 | 35 | 35 |
| Present process (Example-3) | 97.5 |  | 2.5 |

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the specification appended hereto.

We claim:
1. A process for preparation of 2-amino-5-hydroxy propiophenone of Formula I,

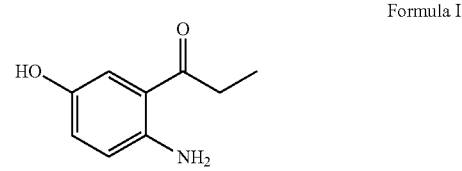

comprising:
  a) reacting a compound of Formula III with a suitable nitrating reagent to obtain a compound of Formula IV,

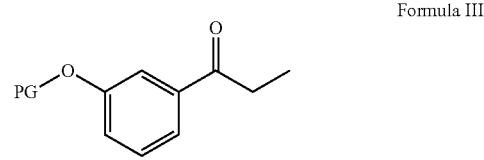

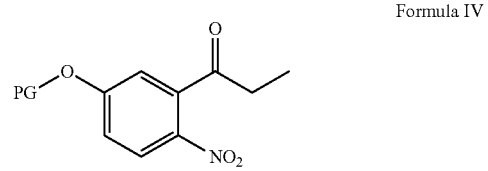

wherein "PG" represents a suitable hydroxyl protecting group; and
  b) converting the compound of Formula IV into the 2-amino-5-hydroxy propiophenone of Formula I.

2. The process as claimed in claim 1, wherein the hydroxyl protecting group is selected from the group consisting of trichloroethyl formate, methyl formate, ethyl formate, hexyl formate, isobutyl formate, benzyl formate, methoxymethyl, methoxyethoxymethyl, tetrahydropyranyl, tetrahydrofuran, allyl, methoxytrityl, methylthio methyl, benzyl, benzoyl, p-methoxybenzyl, t-butyldimethylsilyl, t-butyldiphenylsilyl, triisopropylsilyl, di-tert-butylsilylene, tetraisopropyldisiloxanylidene, pivaloyl, and benzoyl.

3. The process as claimed in claim 2, wherein the hydroxyl protecting group is one of trichloroethyl formate, ethyl formate, or hexyl formate.

4. The process as claimed in claim 1, wherein the nitrating reagent is selected from the group consisting of a nitrating mixture, sodium nitrate, potassium nitrate, calcium nitrate, cupric nitrate, and mixtures thereof, wherein the nitrating mixture is a mixture of nitric acid and sulfuric acid.

5. The process as claimed in claim 4, wherein the nitrating reagent is one of the nitrating mixture or the potassium nitrate.

6. The process as claimed in claim 1, wherein the step a) is carried out in a suitable solvent and optionally in the presence of an acid.

7. The process as claimed in claim 6, wherein the solvent is selected from the group consisting of methylene chloride, ethylene chloride, chloroform, toluene, xylene, dimethyl formamide, dimethyl acetamide, dimethyl sulfoxide, N-methyl pyrrolidinone, acetonitrile, propionitrile, and mixtures thereof.

8. The process as claimed in claim 6, wherein the acid is selected from the group consisting of hydrochloric acid, hydrobromic acid, sulfuric acid, perchloric acid, phosphoric acid, acetic acid, acetic anhydride, trifluoro acetic acid, trichloro acetic acid, methane sulfonic acid, and mixtures thereof.

9. A process for preparation of 2-amino-5-hydroxy propiophenone of Formula I,

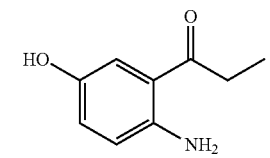

Formula I comprising:
a) reacting a compound Formula II with a suitable hydroxyl protecting agent to obtain a compound of Formula III,

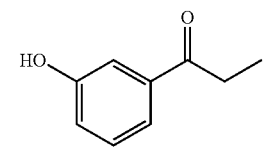

Formula II

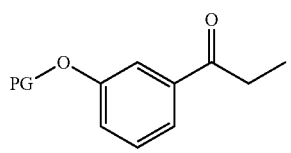

Formula III wherein "PG" represents a suitable hydroxyl protecting group;
b) reacting the compound of Formula III with a suitable nitrating reagent to obtain a compound of Formula IV,

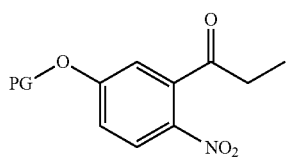

Formula IV c) deprotecting the compound of Formula IV with a suitable deprotecting agent to obtain a compound of Formula V,

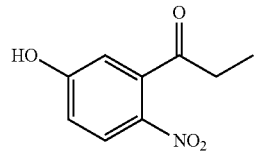

Formula V and
d) reducing the compound of Formula V with a suitable reducing agent to obtain 2-Amino-5-hydroxy propiophenone of Formula I or
e) reducing the compound of Formula IV with a suitable reducing agent to obtain a compound of Formula VI,

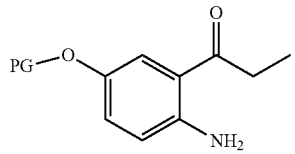

Formula VI and
f) deprotecting the compound of Formula VI with a suitable deprotecting agent to obtain the 2-amino-5-hydroxy propiophenone of Formula I.

10. The process as claimed in claim 9, wherein the hydroxyl protecting agent is selected from the group consisting of trichloroethyl chloroformate, methyl chloroformate, ethyl chloroformate, hexyl chloroformate, isobutyl chloroformate, benzylchloroformate, methoxymethylchloride, methoxyethoxy methylchloride, tetrahydropyranyl ether, allyl bromide, methoxytrityl chloride, methylthioethyl chloride, benzyl bromide, benzoyl bromide, p-methoxybenzyl chloride, t-butyldimethylsilyl chloride, t-butyldiphenylsilyl chloride, triisopropylsilyl chloride, di-tert-butylsilylene chloride, tetraisopropyl disiloxanylidene chloride, pivaloyl chloride, and benzoyl chloride.

11. The process as claimed in claim 9, wherein the hydroxyl protecting group is selected from the group consisting of trichloroethyl formate, methyl formate, ethyl formate, hexyl formate, isobutyl formate, benzyl formate, methoxymethyl, methoxyethoxymethyl, tetrahydropyranyl, tetrahydrofuran, allyl, methoxytrityl, methylthio methyl, benzyl, benzoyl, p-methoxybenzyl, t-butyldimethylsilyl, t-butyldiphenylsilyl, triisopropylsilyl, di-tert-butylsilylene, tetraisopropyldisiloxanylidene, pivaloyl, and benzoyl.

12. The process as claimed in claim 9, wherein the hydroxyl protecting group is one of trichloroethyl formate, ethyl formate, or hexyl formate.

13. The process as claimed in claim 9, wherein the hydroxyl protecting agent is one of trichloroethyl chloroformate, ethyl chloroformate, or hexyl chloroformate.

14. The process as claimed in claim 9, wherein the step a) is carried out in presence of a suitable base and a suitable solvent.

15. The process as claimed in claim 14, wherein the base is selected from the group consisting of sodium hydroxide, potassium hydroxide, sodium hydride, potassium hydride, sodium amide, potassium amide, lithium amide, sodium methoxide, sodium ethoxide, sodium t-butoxide, potassium t-butoxide, sodium carbonate, potassium carbonate, cesium carbonate, sodium bicarbonate, potassium bicarbonate, sodium phosphate, trisodium phosphate, potassium phosphate, tripotassium phosphate, ammonium carbonate, triethylamine, tri-n-propylamine, tri-n-butylamine, methyldibutylamine, diisopropylamine, diisopropylethylamine, dicyclohexylamine, methyl dicyclohexylamine, ethyldiisopropyl amine, N,N-diethyldicyclohexylamine, pyridine, dimethylamino-4-pyridine, N-methyl piperidine, N-ethylpiperidine, N-ethylpiperidine, N-butylpiperidine, 1,2-dimethyl piperidine, or mixtures thereof.

16. The process as claimed in claim 14, wherein the solvent is selected from the group consisting of acetone, methyl ethyl ketone, methyl isobutyl ketone, diethyl ketone, acetonitrile, propionitrile, diethyl ether, tetrahydrofuran, methyl tetrahydrofuran, 1,4-dioxane, dimethylacetamide, dimethylformamide, dimethylsulfoxide, N-methylpyrrolidone, methylene chloride, ethylene chloride, chloroform, toluene, xylene, water, or mixtures thereof.

17. The process as claimed in claim 9, wherein the nitrating reagent is selected from the group consisting of nitrating mixture, sodium nitrate, potassium nitrate, calcium nitrate, cupric nitrate, and mixtures thereof, wherein the nitrating mixture is a mixture of nitric acid and sulfuric acid.

18. The process as claimed in claim 17, wherein the nitrating reagent is the nitrating mixture or potassium nitrate.

19. The process as claimed in claim 9, wherein the step b) is carried out in a suitable solvent optionally in presence of an acid.

20. The process as claimed in claim 19, wherein the solvent is selected from the group consisting of methylene chloride, ethylene chloride, chloroform, toluene, xylene, dimethyl formamide, dimethyl acetamide, dimethyl sulfoxide, N-methyl pyrrolidinone, acetonitrile, propionitrile, and mixtures thereof.

21. The process as claimed in claim 19, wherein the acid is selected from the group consisting of hydrochloric acid, hydrobromic acid, sulfuric acid, perchloric acid, phosphoric acid, acetic acid, acetic anhydride, trifluoro acetic acid, trichloro acetic acid, methane sulfonic acid, and mixtures thereof.

22. The process as claimed in claim 19, wherein the solvent is methylene chloride and the acid is sulfuric acid.

23. The process as claimed in claim 9, wherein the deprotecting agent used in step c) or step f) is selected from the group consisting of lithium hydroxide, sodium hydroxide, potassium hydroxide, sodium methoxide, sodium ethoxide, sodium tert-butoxide, potassium tert-butoxide, sodium carbonate, potassium carbonate, cesium carbonate, sodium bicarbonate, potassium bicarbonate, triethylamine, isopropyl ethylamine, diisopropyl amine, diisopropyl ethylamine, N-methyl morpholine, piperidine, pyridine, hydrochloric acid, hydrobromic acid, boron tribromide, trimethylsilyl iodide, zinc bromide, titanium(IV) chloride, 2,3-dichloro-5,6-dicyanobenzoquinone, and mixture thereof.

24. The process as claimed in claim 23, wherein the deprotecting agent used in step c) and f) is potassium carbonate.

25. The process as claimed in claim 9, wherein the step c) and step f) are carried out in a suitable solvent, wherein the solvent is selected from the group consisting of methanol, ethanol, isopropanol, n-butanol, methylene chloride, ethylene chloride, chloroform, dimethyl formamide, dimethyl acetamide, dimethyl sulfoxide, N-methyl pyrrolidinone, acetonitrile, propionitrile, formic acid, acetic acid, and mixtures thereof.

26. The process as claimed in claim 25, wherein the solvent used in step c) and step f) is methanol.

27. The process as claimed in claim 9, wherein the reducing agent used in step d) or step e) is selected from the group consisting of iron in HCl, iron/NH$_4$Cl, SnCl$_2$, sodium dithionite, sodium hydrosulfite, tin (II) chloride, titanium (III) chloride, zinc/NH$_4$Cl, zinc/hydrazine hydrate, iron/hydrazine hydrate, raney nickel, and mixtures thereof.

28. The process as claimed in claim 27, wherein the reducing agent used in step d) and step e) is sodium dithionite.

29. The process as claimed in claim 9, wherein the step d) and step e) are carried out in a solvent, wherein the solvent is selected from the group consisting of methanol, ethanol, isopropanol, n-butanol, methylene chloride, ethylene chloride, acetonitrile, propionitrile, water, and mixtures thereof.

30. The process as claimed in claim 29, wherein the solvent used in step d) and step e) is water.

31. A process for the preparation of irinotecan, which comprises:
preparing a compound of Formula I according to claim 1 and converting the compound of Formula I into 7-ethyl-10-hydroxycamptothecin (SN-38); and
converting the 7-ethyl-10-hydroxycamptothecin to Irinotecan.

* * * * *